United States Patent [19]

Pocknell

[11] Patent Number: 4,888,074
[45] Date of Patent: Dec. 19, 1989

[54] THERAPEUTIC RINGS

[75] Inventor: David Pocknell, Antibes, France

[73] Assignee: Dow Corning France S.A., Valbonne, France

[21] Appl. No.: 222,441

[22] Filed: Jul. 21, 1988

[30] Foreign Application Priority Data

Jul. 22, 1987 [FR] France ................ 87 10363

[51] Int. Cl.4 ............ B29C 47/06; B29C 53/62; B32B 25/20; B32B 31/18
[52] U.S. Cl. ............... 156/217; 156/256; 264/151; 264/152; 264/171; 264/210.2; 264/236; 264/281; 264/295; 264/331.11; 264/339; 424/432; 604/892.1
[58] Field of Search ........... 264/151, 152, 159, 171, 264/210.2, 236, 281, 295, 320, 331.11, 339, DIG. 40; 156/217, 244.12, 144.18, 144.24, 256; 424/432; 128/833; 604/54, 55, 57, 892.1

[56] References Cited

U.S. PATENT DOCUMENTS

| | | | |
|---|---|---|---|
| 2,432,870 | 12/1947 | Evalt | 264/281 X |
| 2,459,721 | 1/1949 | Poltorak | 156/217 X |
| 2,670,313 | 2/1954 | Young | 156/217 X |
| 2,852,424 | 9/1958 | Reinhart et al. | 264/281 X |
| 3,026,569 | 3/1962 | Keller | 264/152 X |
| 3,068,531 | 12/1962 | Love | 264/281 X |
| 3,586,566 | 6/1971 | Van Vleet et al. | 156/256 X |
| 3,710,795 | 1/1973 | Higuchi et al. | 604/892.1 |
| 3,920,805 | 11/1975 | Roseman | 424/432 |
| 4,012,496 | 3/1977 | Schopflin et al. | 424/432 |
| 4,050,975 | 9/1977 | Draffone | 156/217 |
| 4,182,738 | 1/1980 | Casaert et al. | 264/210.2 |
| 4,720,384 | 1/1988 | DiLuccio et al. | 264/171 X |

FOREIGN PATENT DOCUMENTS

| | | | |
|---|---|---|---|
| 1121153 | 10/1984 | U.S.S.R. | 264/152 |
| 1412969 | 11/1975 | United Kingdom . | |
| 1528602 | 10/1978 | United Kingdom . | |
| 1581474 | 12/1980 | United Kingdom . | |

Primary Examiner—Jeffery Thurlow
Assistant Examiner—Leo B. Tentoni
Attorney, Agent, or Firm—Susan M. Cornwall; Allan O. Maki

[57] ABSTRACT

The specification describes and claims a method of making therapeutic rings from a curable silicone rubber based composition. The rings are capable of controlled release of the therapeutic agent in the human or animal body. The method includes the steps of:
(i) extruding a first composition comprising a therapeutic agent and a first elastomer-forming silicone composition to provide a core;
(ii) extruding a second composition comprising a second elastomer-forming silicone composition to provide a sheath enclosing the core;
(iii) bringing together end portions of a piece of extruded core and sheath to form a ring,
(iv) effecting crosslinking of the extruded core, and
(v) effecting crosslinking of the extruded sheath.

12 Claims, 3 Drawing Sheets

THERAPEUTIC RINGS

This invention is concerned with therapeutic rings and particularly with the manufacture thereof.

Products are known which are capable of use on or in the human or animal body to release therapeutic agents to the body at a controlled, desired rate to provide treatment over a prolonged period. Proposals have been made to use various therapeutic agents in this way, for example digitoxin, isoproterenol, atropine, histamine, pyrimethamine, hormonal substances e.g. oestrogenic substances, progestational substances, androgenic substances, for example estradiol, progesterone, androstenedione, testosterone, cortisol and chlormadinone.

It is known to provide for example products formed from non-toxic resilient polymer and contraceptive medication releaseable therefrom which are in the form of a ring and are intended for insertion in the vagina of a human or animal body. In one proposed method of manufacture, silicone products are employed for the manufacture of such rings which are cast in a multi-step procedure. U.S. Patent Specification No. 3 920 805 describes the manufacture of a solid pharmaceutical device formed as a vaginal ring consisting essentially of a non-medicated central core and an encircling finite thickness of a medicated coating which involves (1) placing a siloxane and catalyst mixture into two halves of a mould to provide a so-called centered polymeric core, tightening the mould and curing the siloxane mixture: (2) placing the polymeric core into one half of its mould, filling one half of an outer mould with a medicated polymeric siloxane mixture containing a catalyst, placing the filled one half over the core of the first step and curing: (3) after the mould of the second step is cured filling the other half of the outer mould with the catalysed and medicated polymeric siloxane mixture, bonding this half plus the cured half of the second step together and the whole is cured again. This method requires several manipulations of the ring as it is formed and is relatively labour intensive. Rings made by this method require a trimming of the sprue and of the edges where the two halves of the outer part of the ring are joined, as such edges may cause irritation when the ring has been placed in the body.

In order to control the release rate of therapeutic agents from a ring, it is desirable to have the medication in the core of the ring surrounded by a sheath of non-medicated material. It is of utmost importance to control the centralisation of the core in the ring, in order to ensure the correct release rate.

G.B. Patent Specification No. 1 412 969 is directed to preparations comprising silicone rubber carriers and pharmacologically active substances which carriers are intended to permit a regular invariable and long lasting release of pharmacologically active substance. The silicone rubber carriers are formed from silicone rubber of the so-called LTV type i.e. low temperature vulcanising. G.B. Patent Specification Nos. 1 528 602 and 1 581 474 are directed to rings of defined structural characteristics made by use of for example the so-called LTV silicone rubbers.

It is an object of the invention to provide an improved method of making a ring capable of the controlled release of therapeutic agents in the human or animal body.

The present invention provides in one of its aspects a method of making a ring capable of the controlled release of a therapeutic agent in the human or animal body comprising the following steps namely:

(i) extruding a first composition comprising a therapeutic agent and a first elastomer-forming silicone composition to provide a core, (ii) extruding a second composition comprising a second elastomer-forming silicone composition to provide a sheath enclosing the core, (iii) bringing together end portions of a piece of the extruded core and sheath to form a ring.

(iv) effecting crosslinking of the extruded core and (v) effecting crosslinking of the extruded sheath.

In a method according to the invention, the first elastomer-forming silicone composition may be an organosilicon compound capable of crosslinking with or without the presence of crosslinking agents. Such crosslinking may be performed at elevated or at ambient temperatures. The elastomer-forming silicone composition may crosslink only very slowly at room temperature and have a greatly increased crosslinking rate at elevated temperatures of the order of 70 to 110° C. The organopolysiloxanes used are such that the composition is shape retaining and capable of extrusion and is also resistant to flow after extrusion and before crosslinking has fully developed. Elastomer-forming silicone compounds comprising organopolysiloxanes having silicon-bonded hydroxyl groups which may be crosslinked to elastomers by the addition of a crosslinking agent and a condensation catalyst may be used, although they are not preferred. In such compounds the organopolysiloxane is generally a polydiorganosiloxane having terminal silanol groups. The crosslinking agent may be for example an alkoxy silane or an alkyl polysilicate e.g. methyl trimethoxysilane or ethyl polysilicate, or it may be an alkylhydrogen polysiloxane e.g. a polymethylhydrogensiloxane. A variety of catalysts may be employed, the organic metal compounds e.g. stannous octoate, dibutyltin dilaurate, alkyl titanates and titanium chelates being illustrative of these. Such elastomer-forming compounds are well known in the art and have been described in for example British Patent Nos. 841 825, 844 128, 957 255 and 962 061. Such compositions are not among preferred ones for use in the present invention as volatile by-products of the crosslinking action are likely to lead to voids in the rings unless suitably controlled. Also, the tin catalysts employed in such compositions are less favoured from a toxicity viewpoint. Preferred elastomer-forming silicone compositions are those which crosslink, for example upon heating, without production of volatile by-products. Not only does the absence of volatile by-products simplify the manufacturing process but also, such compositions show little or no alteration in volume during crosslinking. This permits a more accurate manufacture of the rings with respect to their shape and size. Thus peroxide containing compositions which crosslink through a free radical mechanism when irradiated or heated may be used. Due to the possibility to formulate compositions which crosslink at lower temperatures, as may be desirable when certain therapeutic agents are employed, the most preferred compositions are those silicone compositions which crosslink through reaction of unsaturated groups and which comprise one or more organopolysiloxanes having per molecule at least two silicon-bonded groups having aliphatic unsaturation, an organosilicon compound having at least two silicon-bonded hydrogen atoms and a catalyst e.g. a platinum compound or complex which promotes the reaction between unsaturated groups and silicon-bonded hydrogen groups. The aliphatically unsaturated groups are preferably olefinically unsaturated. The organopolysiloxane used in such a composition typically is a high molecular weight polysiloxane of gum like consistency and comprises units of the general formula $$Q_a Q'SiO_{\frac{3-a}{2}} \text{ and } Q_b SiO_{\frac{4-b}{2}},$$

wherein Q denotes a monovalent hydrocarbon or substituted hydrocarbon group having no more than 8 carbon atoms, for example a methyl or a phenyl group, Q' denotes an organic group having olefinic unsaturation, preferably being a vinyl or allyl group, at least 80% of the remaining silicon-bonded substituents being methyl, has a value of 1 or 2 and b has a value of 0, 1, 2 or 3. The organosilicon compound used in such a composition is typically an organohydrogensiloxane having a viscosity up to about 50 mm$^2$/s and having at least 2 silicon-bonded hydrogen atoms per molecule and the remaining silicon-bonded substituents being monovalent hydrocarbon groups having no more than 8 carbon atoms, preferably being methyl groups. The platinum containing compound or complex is for example chloroplatinic acid, platinum acetylacetonate, a complex of platinous halides with unsaturated compounds such as ethylene, propylene, organovinylsiloxanes and styrene, methyldiplatinum and Pt(CN)$_3$. The composition may and preferably does include a catalyst inhibitor, for example an alkynyl compound such as an acetylenically unsaturated secondary or tertiary alcohol for example ethynyl cyclohexanol. The ingredients of the composition are chosen so that the composition cures at temperatures below about 120° C. and so that the cured elastomer has a durometer hardness in the range 20 to 60, more preferably about 35. Compositions of this type are well known in the art (see for example British Patent Specifications Nos. 1 090 122, 1 141 868 and 1 409 223) and are commercially available. The elastomer-forming compositions may also comprise other ingredients, for example fillers and plasticisers.

The therapeutic agents used in a method according to the invention may be any pharmaceutically active material which can usefully be administered at a low dosage over a long period of time and may be for example an antiseptic, antibiotic, antifungal, antiviral or contraceptive agent or a histamine, atropine or hormonal substance. Examples of suitable therapeutic agents are oestradiol, progesterone, andristenedione, testosterone, levonogestrone, cortisol, medoxyprogesterone acetate or melengestrol acetate. Such agents may be incorporated in the first composition according to standard methods known in the art. These agents may for example be mixed with the first elastomer-forming silicone composition or with a part thereof e.g. with part of the organopolysiloxane compound used in the composition, prior to incorporating that part into the first composition. The concentration of the therapeutic agent employed in the composition, the size of the core and the size of the surrounding sheath, are selected to provide the required release rate of the agent and the required useful lifetime of the ring, i.e. the time that the ring will be capable of releasing the therapeutic agent at the required rate. The concentration of the therapeutic agent may vary according to the agent used from less than 0.1% by weight to more than 30% by weight of the first composition. The composition may be extruded using conventional extrusion methods and equipment. The diameter of the core may vary depending on the required rate of release and the type of therapeutic agent employed. The core may, for example, have a diameter of from 2 to 6 mm.

In step (ii) of a method according to the invention a composition comprising a second elastomer-forming silicone composition is extruded onto the core. This composition may be any of those elastomer-forming composition referred to under step (i), and is preferably the same composition as used in step (i), in order to maximise compatibility between the core and the sheath. The sheath may be extruded onto the core after the latter has been extruded, but is preferably extruded simultaneously with the core. Using this co-extrusion technique the positioning of the core inside the sheath can be sufficiently controlled, keeping it consistent throughout the manufacture. Preferably the core and the sheath are kept substantially concentric. The extruded core and sheath are of sufficiently cohesive strength to retain their shape.

In step (iii) of a method according to the invention end portions of a piece of the extrudate, which comprises both the core and the sheath, are brought together to form a ring. Pieces of extrudate of a length appropriate to form a ring of desired size may be provided by extruding a length which is substantially the required circumference of the ring, or by extruding a longer section which may be divided up into individual pieces of the required length, for example by cutting the extrudate. End portions of a piece may be brought together for example by placing the piece in a mould which has a ring form, so that the end portions are in contact with each other or with means for fixing the portions together. Such means include for example a suitable adhesive compound or a layer of uncured elastomer-forming composition which can crosslink with the second, and preferably with both the first and the second elastomer-forming silicone compositions used in the method. We prefer to arrange that each piece of extrudate has developed sufficient "structure" to ensure that the necessary handling of the extrudate during shaping thereof into the form of a ring does not damage it due to its inherent softness. Deformation of the sheath or core, changing their ring configuration, is undesirable because it is desirable that the manufactured rings have a consistent shape so that they are able to deliver the therapeutic agent in a predictable and consistent manner. This "structure" may be obtained by the addition to the first and/or second composition of an additive causing thixotropy, but preferably the second elastomer-forming silicone composition and more preferably both first and second elastomer-forming silicone compositions of each piece are at least partially polymerised prior to the transfer to the mould and the shaping of the extrudate in an annular shape. It is also preferred to form the end portions of each piece in such a way that there is a minimum of strain on the extrudate during the bringing together of the end portions to form the ring. This may be achieved by cutting the end portions of a straight extrudate at an angle to the parallel, so that their end surfaces may contact each other over substantially their whole surface area, for example when placed in the mould.

In steps (iv) and (v) of a method according to the invention crosslinking is effected of the extruded core and sheath respectively. In a preferred method steps (iv)

and (v) are carried out simultaneously. This crosslinking or curing step may take place at ambient or elevated temperatures, depending on the type of elastomer-forming composition used in the extrusion steps (i) and (ii). Care must be taken to keep the temperature below that at which the therapeutic agent degrades. The crosslinking may be effected after the step (iii) in which the end portions are brought together. In another of the aspects of the method the extruded core and sheath are crosslinked before step (iii) of the process is reached. In yet another of its aspects the crosslinking of the extruded core and sheath causes the securing of the end portions of the extrudate brought together during step (iii). The fourth and fifth steps of a method according to the invention may be effected in one or in several parts. In a preferred method, the extrudate is allowed to partially crosslink before step (iii) of a method according to the invention to allow the extrudate to gain "structure" before cutting the extrudate to the right length, followed by a further crosslinking at or after step (iii).

Using a method according to the invention has the advantage that one may produce rings of at least substantially consistent quality in a simple way.

In a preferred method of making the rings the extrudate is shaped in such a way that only a minor alteration is required to obtain the ring form. We have found that this can be achieved by shaping the extrudate in a helical form.

A method according to the preceding paragraph is conveniently performed by shaping the extrudate which is formed according to steps (i) and (ii) of a method according to the invention on a mandrel having a helically shaped receptive surface portion. The mandrel may be rotated whilst the extrudate is continually fed onto it. The mandrel and the extrusion head may be moved sideways in relation to each other in order to allow continuous collection of the extrudate on the mandrel. Individual turns may be detached from the helix singly or in groups preferably when the extrudate has gained sufficient "structure". Other aspects of the method, e.g. with regard to crosslinking as described above also apply to the preferred method described here.

This preferred method has a number of additional advantages. These include the possibility to cut a plurality of pieces of extrudate required for the formation of the rings with one cutting action; the fact that the extrudate is already in a substantially annular shape and, therefore, very little strain is exercised on the extrudate in bringing the end portions together; the fact that a simple straight cut is possible as this will permit the opposed end portions to contact each other over substantially the complete surface area of the end portions; the possibility of curing the extrudate before it is cut in pieces of the required length; and the possibility of using a multiple mould into which a plurality of detached individual turns may be placed in order to polymerise them in the ring shape simultaneously.

The invention also provides a method of making a ring capable of the controlled release of a therapeutic agent in the human or animal body comprising the following steps namely:

(i) extruding a first composition comprising a therapeutic agent and a first elastomer-forming silicone composition to provide a core;

(ii) extruding a second composition comprising a second elastomer-forming silicone composition to provide a sheath enclosing the core;

(iii)a shaping the extruded core and sheath as a helix comprising a plurality of turns;

(iii)b detaching an individual turn from the helix;

(iii)c bringing together end portions of the turn to form a ring, (iv) effecting crosslinking of the extruded core, and (v) effecting crosslinking of the extruded sheath.

In a method according to the present invention the extrusion method causes no sprue on the wall of the extrudate which has to be removed from the rings, and the end portions of the ring are fixed together in such a way that the join is substantially normal to the plane of the ring and thus, at most, only a single ring of "flash" may be obtained. The area which might need trimming in order to smooth the surface of the ring is thus small.

The invention provides in another of its aspects a ring capable of the controlled release of a therapeutic agent in the human or animal body made by a method according to the invention.

There now follows a description of two illustrative methods according to the invention and of the rings formed by those methods, which is to be read together with the accompanying figures. All parts and percentages are expressed by weight unless otherwise stated.

Figure 1:
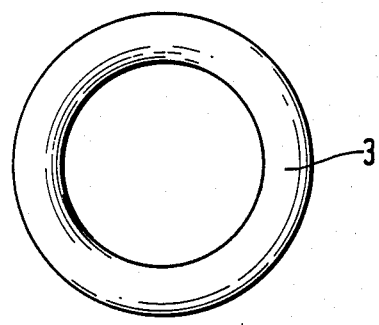
FIG. 1 is a plan view of a ring according to the invention.
Figure 2:
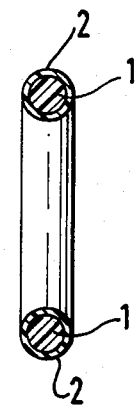
FIG. 2 is a sectional view of a piece of the ring of FIG. 1.

A first elastomer-forming silicone composition capable of curing to provide an elastomer of about 35 Durometer was prepared by mixing 50 parts of a mixture A which consisted of 72.4 parts of a high molecular weight polyorganosiloxane having vinyl functional groups on about 0.2% of the silicon atoms, 25.5 parts of a silica filler, 0.1 part of ethynylcyclohexanol and 2 parts of a low molecular weight organosilicon material, namely a copolymer of polydimethyl and polymethyl hydrogen siloxanes, having silicon-bonded hydrogen atoms, and 50 parts of a mixture B which consisted of 73.75 parts of a high molecular weight polyorganosiloxane having vinyl functional groups on about 0.2% of the silicon atoms, 25.9 parts of a silica filler and 0.35 part of a platinum containing catalyst. A therapeutic agent base was prepared by mixing 10 parts of levonogestrone and 90 parts of a vinyl functional polydiorganosiloxane. A first composition was prepared comprising 10 parts of the therapeutic agent base, 20 parts of $BaSO_4$ and 970 parts of the first elastomer-forming silicone composition. A second composition was prepared by taking 1000 parts of the first elastomer-forming silicone composition.

1.5 kg of each of the first and second compositions were loaded to a first and second chamber respectively of a crosshead extruder and the extruder was regulated such that a continuous extrudate was obtained, comprising a core (1) with a diameter of 2 mm consisting of the first composition and a sheath (2), consisting of the second composition, giving the extrudate an overall diameter of 9 mm.

Figure 3:
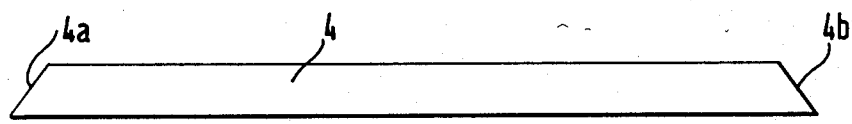
FIG. 3 is an elevation of a cylindrical linear piece of extrudate (comprising an extruded core and sheath) of a length appropriate to form a vaginal ring and having end surfaces inclined at opposing angles to the axis of the extrudate.
Figure 4:
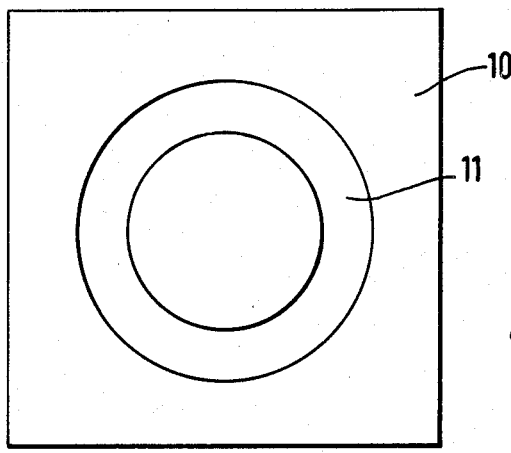
FIG. 4 is a plan view of a half mould for shaping the ring.
Figure 5:
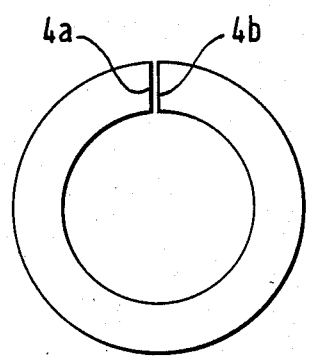
FIG. 5 is a view of the piece of extrudate of FIG. 3 curled to form a ring having its end surfaces juxtaposed just prior to their disposition in mating contact.

In a first illustrative method a length of about 1 m of the extrudate was extruded onto a flat support where it was kept overnight at room temperature. After this time sufficient crosslinking had taken place to give the extrudate sufficient "structure". It was then cut with a sharp blade into pieces (4) (FIG. 3) having a length of about 173 mm at an angle of 45° exposing end surfaces (4a) and (4b). The piece (4) was then transferred to a half mould (10) (FIG. 4) having a ring shaped cavity (11) into which the piece (4) was curled, bringing its end surfaces (4a, 4b) in juxtaposition as shown in FIG. 5, before bringing them into full contact with each other. In this disposition the crosslinking of the first and second compositions could effect crosslinking across the contact line of the two end surfaces. A complementary half mould to (10) was then placed on top of the half mould (10) and the mould was closed. This was then placed in an oven at 100° C. for 5 minutes to further crosslink the elastomer-forming silicone composition of the core and sheath. The mould was then allowed to cool, opened and the ring produced (3) was taken out from the mould showing only a slight mark where the two end surfaces had met.

Figure 6:
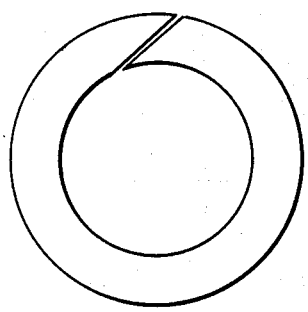
FIG. 6 is a view of a piece of extrudate curled to form a ring having its end surfaces inclined at alternative angles to those of FIG. 3, juxtaposed prior to their disposition in mating contact.
Figure 7:
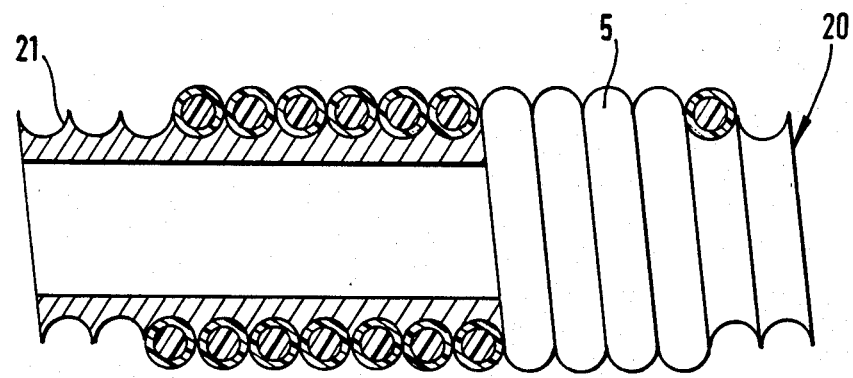
FIG. 7 is a diagrammatic view partly in section showing collection of extrudate in helical configuration upon a helically shaped receptive surface of a mandrel.

In a second illustrative method a length of continuous extrudate, prepared and obtained as described above, was delivered onto a mandrel (20) (FIG. 7) with a diameter of 37 mm having a helically shaped receptive surface portion (21). The mandrel was turned at a speed of 10 rpm shaping the extrudate in helical form (5). When the mandrel (20) was full, having a plurality of turns, the extrusion onto it was discontinued and the mandrel (20) with the extrudate was placed in an oven at 100° C. for about 5 minutes in order to crosslink the extrudate. After it had cooled the crosslinked helical extrudate (5) was cut along the length of the mandrel (20) in one cutting action using a sharp blade. The individual turns thus obtained were detached and placed in moulds (10). The cutting action yielded turns as shown in FIG. 5 but cutting could also be done at an angle to the radius of the mandrel, yielding turns which are illustrated in FIG. 6. A small disc of the first elastomer-forming silicone composition was placed in contact with the end surfaces of each individual turn. The mould was then closed and the method continued as in the first illustrative method.

What is claimed is:

1. A method of making a ring capable of the controlled release of a therapeutic agent in a body comprising the following steps namely:
   (i) extruding a first composition comprising a therapeutic agent and a first elastomer-forming silicone composition to provide a core;
   (ii) extruding a second composition comprising a second elastomer-forming silicone composition to provide a sheath enclosing the core;
   (iii) bringing together end portions of a piece of extruded core and sheath to form a ring,
   (iv) effecting crosslinking of the extruded core, and
   (v) effecting crosslinking of the extruded sheath.

2. A method according to claim 1 wherein the sheath is extruded simultaneously with the core.

3. A method according to claim 1 wherein crosslinking of the extruded core and of the sheath is commenced before step (iii).

4. A method according to claim 1 wherein crosslinking of the extruded core and sheath causes securing of the end portions brought together during step (iii).

5. A method according to claim 1 wherein crosslinking of the extruded core and sheath is effected prior to step (iii).

6. A method according to claim 1 wherein the first and second elastomer-forming silicone compositions are heated to accelerate their crosslinking.

7. A method according to claim 1 wherein the first and second elastomer-forming silicone compositions comprise an organopolysiloxane having per molecule at least two silicon-bonded groups having olefinic unsaturation, an organosilicon compound having per molecule at least two silicon-bonded hydrogen atoms and a catalyst which promotes the reaction between olefinic groups and silicon-bonded hydrogen groups.

8. A method according to claim 1 wherein the therapeutic agent is a contraceptive agent.

9. A method according to claim 8 wherein the contraceptive agent is oestradiol or levonogesterone.

10. A method of making a ring capable of the controlled release of a therapeutic agent in a body comprising the following steps namely:
    (i) extruding a first composition comprising a therapeutic agent and a first elastomer-forming silicone composition to provide a core;
    (ii) extruding a second composition comprising a second elastomer-forming silicone composition to provide a sheath enclosing the core;
    (iii)a shaping the extruded core and sheath as a helix comprising a plurality of turns;
    (iii)b detaching an individual turn from the helix;
    (iii)c bringing together end portions of the turn to form a ring,
    (iv) effecting crosslinking of the extruded core, and
    (v) effecting crosslinking of the extruded sheath.

11. A method according to claim 10 wherein the extruded core and sheath are shaped as a helix by extruding onto a mandrel, having a helically shaped receptive surface portion which rotates whilst the extruded core and sheath are continually fed onto it.

12. A method according to claim 10 wherein a plurality of individual turns is detached from the helix by one cutting action.

* * * * *